United States Patent [19]
Haystead et al.

[11] Patent Number: 5,686,310
[45] Date of Patent: Nov. 11, 1997

[54] METHOD FOR DETERMINATION OF THE AMOUNT OF EITHER PHOSPHOTYROSINE OR PHOSPHOSERINE IN A PROTEIN

[75] Inventors: Timothy A.J. Haystead; Timothy MacDonald; R. Patrick Fadden, all of Charlottesville, Va.

[73] Assignee: University of Virginia Patent Foundation, Charlottesville, Va.

[21] Appl. No.: 467,717
[22] Filed: Jun. 6, 1995
[51] Int. Cl.$^6$ .................................................. C07K 1/13
[52] U.S. Cl. ........................ 436/86; 436/172; 436/103
[58] Field of Search ........................... 436/86–90, 56, 436/172, 103, 105

[56] References Cited

U.S. PATENT DOCUMENTS

| | | | |
|---|---|---|---|
| 5,185,243 | 2/1993 | Ullman et al. | 436/94 |
| 5,284,558 | 2/1994 | Linhardt et al. | 436/94 |

OTHER PUBLICATIONS

BIOSIS 95:166168, Fadden et al. (abstract only), 1995.
BIOSIS 92:68405, Byford (abstract only), 1992.
BIOSIS 88:393314, Odani et al. (abstract only), 1988.

*Primary Examiner*—Lyle A. Alexander
*Attorney, Agent, or Firm*—Oblon, Spivak, McClelland, Maier & Neustadt, P.C.

[57] ABSTRACT

Traditional methods for measuring the phosphorylation state of cellular proteins have relied on $^{32}$P-orthophosphate labeling of cells in culture. The problems associated with radioactive isotopes have therefor prohibited phosphorylation studies on whole animals and humans. The present invention provides a unique technique that allows quantitative attachment of probes (e.g. fluorophors or biotin) to phosphoproteins and peptides by activating phospho-amino acids. the phosphorylation state of cellular proteins derived from human tissues can now be measured. This method can be used for early detection of cancer and diabetes and also for the identification of pharmaceutical agents.

12 Claims, 2 Drawing Sheets

METHOD FOR DETERMINATION OF THE AMOUNT OF EITHER PHOSPHOTYROSINE OR PHOSPHOSERINE IN A PROTEIN

BACKGROUND OF THE INVENTION

1. Field of the Invention

The invention relates to a method of quantifying the phosphorylation state of cellular proteins and peptides derived from tissue, a labeled protein and a labeled peptide.

2. Discussion of the Background

The process of reversible protein phosphorylation is recognized as a fundamental mechanism by which the control of cellular regulation is achieved. Indeed, at the current rate of discovery as much as 1% of the human genome may encode protein kinases, the enzymes that catalyze phosphorylation reactions. It has now become clear that the cell utilizes the process of protein phosphorylation as a switching mechanism to control the activity of enzymes and proteins regulating pathways as diverse as metabolism, protein synthesis, gene regulation, cell growth, cell division, to cellular morphology. When a regulatory protein or enzyme is phosphorylated by the appropriate protein kinase it is either activated, inhibited or becomes "marked" for targeting by other regulatory factors.

Approximately 90% of all cellular phosphorylations occur on the amino acid serine, about 9.9% occurs on threonine and only about 0.1% on tyrosine residues. The finding that so few tyrosine phosphorylations occur in cells has been explained by the finding that many hormone receptors are tyrosine kinases (e.g., Insulin and EGF receptors) and that activation of these receptors triggers phosphorylation of many regulatory proteins and enzymes on serine and threonine residues. The precise mechanism by which tyrosine kinases receptors trigger activation of serine/threonine protein kinases has yet to be determined. More importantly, the discovery that many oncogenes encode protein kinase has led to the hypothesis that many disease states, such as cancer and type II diabetes, are the direct result of specific perturbations in tyrosine kinases initiated signal transduction pathways. Therefore, an ability to directly examine protein phosphorylation states in humans, both in normal and pathological states, would be of great medical and diagnostic value in the identification of the causes of these diseases. Furthermore, this ability would be useful as a tool in the discovery and evaluation of new and existing pharmaceutical agents for the treatment of diabetes and cancer.

Traditional methodologies for measuring changes in the phosphorylation state of cellular proteins has relied on the use of $^{32}P$ organic phosphate labeling of isolated cells in culture. Although studying in vitro cellular protein phosphorylation by $^{32}P$ labeling has been tremendously successful for characterizing protein kinase mediated signal transduction pathways, because of the problems associated with use of radioactive isotopes, no useful studies have been carried out on intact tissues, organs, whole animals or humans.

Previously, cellular protein phosphorylation could be measured in two ways. The most popular method is to radiolabel isolated cells in culture with mCi amounts $^{32}P$-orthophosphate. Following radio-labeling, the cells are homogenated and extracts prepared. The extracts are subsequently subjected to either one- or two-dimensional SDS-PAGE and the radio-labeled phospho-proteins characterized by autoradiography following drying of the SDS-gel. This technique requires the use of radioisotopes, which cannot be performed on humans. Autoradiography is also relatively insensitive.

The second method restricts the researcher to examination of proteins containing phosphotyrosine and utilizes commercially available anti-phosphotyrosine antibodies. In this case cell extracts are separated by SDS-PAGE and Western blotted onto nitrocellulose membrane. The blot is then probed with the anti-phosphotyrosine antibody. This technique has the disadvantage of a lack of sensitivity and specificity and is therefore generally prohibitive for analyzing human specimens.

Accordingly, there is a general lack of ability to either qualitatively and quantitatively determine protein phosphorylation states in a biological sample.

SUMMARY OF THE INVENTION

According to one embodiment of the present invention, is a method of determining the amount of phosphoserine in a protein.

According to a second embodiment of the present invention is a method of determining the amount of phosphothreonine in a protein.

According to a third embodiment of the present invention is a method of determining the amount of phosphotyrosine in a protein.

According to a fourth embodiment of the present invention is a method of determining the phosphorylation state of a protein (i.e. phosphorylation state mapping).

These embodiments of the present invention have been made possible by methods of attachment of probes to phosphoproteins and peptides with quantification.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Derivatization of the Phosphoserine With a Thiol Linker

Figure 1:
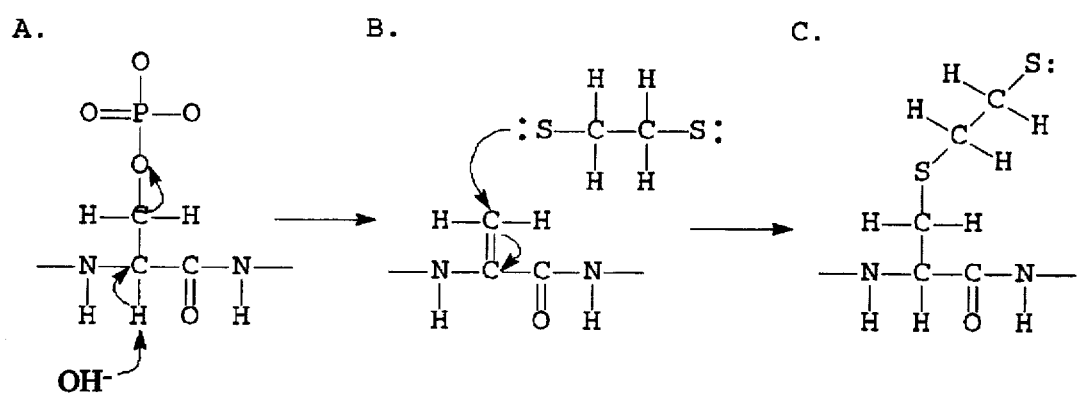
FIG. 1 provides a reaction scheme for derivatizing phosphoserine groups with an alkyldithiol.

Any polyfunctional thiol linking group can be attached to the β-carbon of serine. By the term polyfunctional thiol linking group, it is meant any compound with at least one thiol group and at least one other group capable of reacting with the tag. Suitable groups capable of reacting with the tag are a hydroxyl group, an amino group and a thiol group. Specific non-limiting examples of suitable linking groups are dithiols, trithiols and polythiols, hydroxy thiols such as thio ethylene glycol or thio propylene glycol, amino thiols, and hydroxy-amino thiols. Non-limiting examples of suitable thiol linking groups, are for example an alkyldithiol in which the alkyl group has from 2–12, preferably 2–6 carbon atoms, more preferably ethanedithiol, aryldithiols, alkyl polythiols and arylpolythiols. The alkyl group may be linear or branched, provided that the two thiol groups are separated by at least two carbon atoms. For example, the reaction to substitute an alkyldithiol for the phosphate group on phosphoserine is outlined in FIG. 1. In order for the β-elimination of the phosphate group and activation of alkyldithiol to attack at the β-carbon, there should be a sufficient concentration of hydroxyl ions in the reaction mixture. However, too high a hydroxyl concentration, above the buffering capacity of the alkyldithiol will cause degradation of peptide bonds. The optimal conditions for the β-elimination reaction can be determined by measuring phosphate release as a function of alkyldithiol concentration, at constant NaOH concentration. Alkyldithiol concentrations above 3 molar buffered enough hydroxyl ions to slow phosphate release to an unacceptable level, while alkyldithiol concentrations below 3 molar risked peptide bond degradation. Therefore, all derivatization product of Ala-Thr-SerP-Asn-Val-Phe was analyzed on CZE and depicts a significant change in the peptide's mobility. This derivatization product was confirmed by mass spectrometry (713 Da).

Suitable reaction conditions for attaching the alkyldithiol, are basic conditions, sufficient to induce β-elimination of the phosphate group from the phosphoserine. Suitable bases are alkali and alkaline earth hydroxides. Suitable basis also include alkyl lithiums such as n-butyl lithium, methyl lithium and t-butyllithium, as well as lithium-amide basis such as lithium diisopropylamide. Preferably β-elimination is induced with 5M NaOH, at a pH of ≧12.

Suitable reaction solvents are polar protic solvents such as water, aqueous alcohols such as methanol, ethanol and propanol, as well as polar aprotic solvents such as acetonitrile.

Suitable reaction temperatures are anywhere from 0°–35° C., preferably 25°–27° C.

Fluorescent Tagging of the Derivatized Peptide

The chemistry for coupling 6-iodoacetamidofluoroscein with thiol group is well documented (for example Gurd, F. R. N., (1967), *Methods Enzymol.*, 11, 532–541. Kwok, F., Churchich, J. E., (1980). *J. Biol. Chem.*, 255, 882–888. Parod, R. J., Brain, J. D., (1983), *Am J., Physiol.*, 245, C220–C225)) and the reaction of I-15 with the derivatized peptide was monitored on CZE.

Any group which can react with the reactive termini of a thiol linking group, is suitable to be attached according to the present method. Depending on the intended method of analysis, suitable tags can be fluorescent tags such as fluorescein and measured spectrally, or radioactive and measured appropriately. Particularly suitable tags are fluorescein and biotin.

Analysis of Reaction Efficiencies

The phosphopeptides relative mobility can be obtained by dividing the neutral marker by the peptide's migration time. In this case the neutral marker runs at 4.40 minutes and the peptide at 7.95 minute, giving a relative mobility of 0.53. The amount of sample loaded, 1.416 ng of 1.97 pmol, gives a peak area of 0.61827. The derivatization with EDT shifts the peptide's relative mobility to 0.789. The marginal sample recovery off the Sep-Pak required concentration of the derivatized peptide sample. The peak area, for the derivatized peptide equaled 0.58778 for the same 6 nl injection volume, which suggests only 1.87 pmol in the same sample volume. Sample recovery after passing through the Sep-Pak cartridge was determined to be 33.2%. The addition of I-15 fluorophor to the peptide shifts its relative mobility to 0.601, while reducing the derivatized peptide peak at 5.63 minutes significantly. The peak at 8.49 minutes is due to excess fluorophor in the reaction.

Derivatization of the Phosphotyrosine

The specific identification of phosphotyrosine residues in proteins is faced with several technical challenges. These problems are particularly acute, since tyrosine phosphorylation represents only a small fraction (<<1%) of the total phosphorylated amino acids on proteins and invariably represents a minor contribution to total tyrosine content in proteins. Prominent among the difficulties faced in specific identification of phosphotyrosine residues are: (1) the differentiation from other phosphorylated amino acids (serine, threonine, (histidine)) generally co-occurring in phosphoproteins; and (2) the differentiation from carboxylic acid moieties found in aspartate and glutamate residues and at the C-terminus of the peptide chain, due to similar chemistry with the acidic (O—H) bonds of the phosphate monoester.

Figure 2:
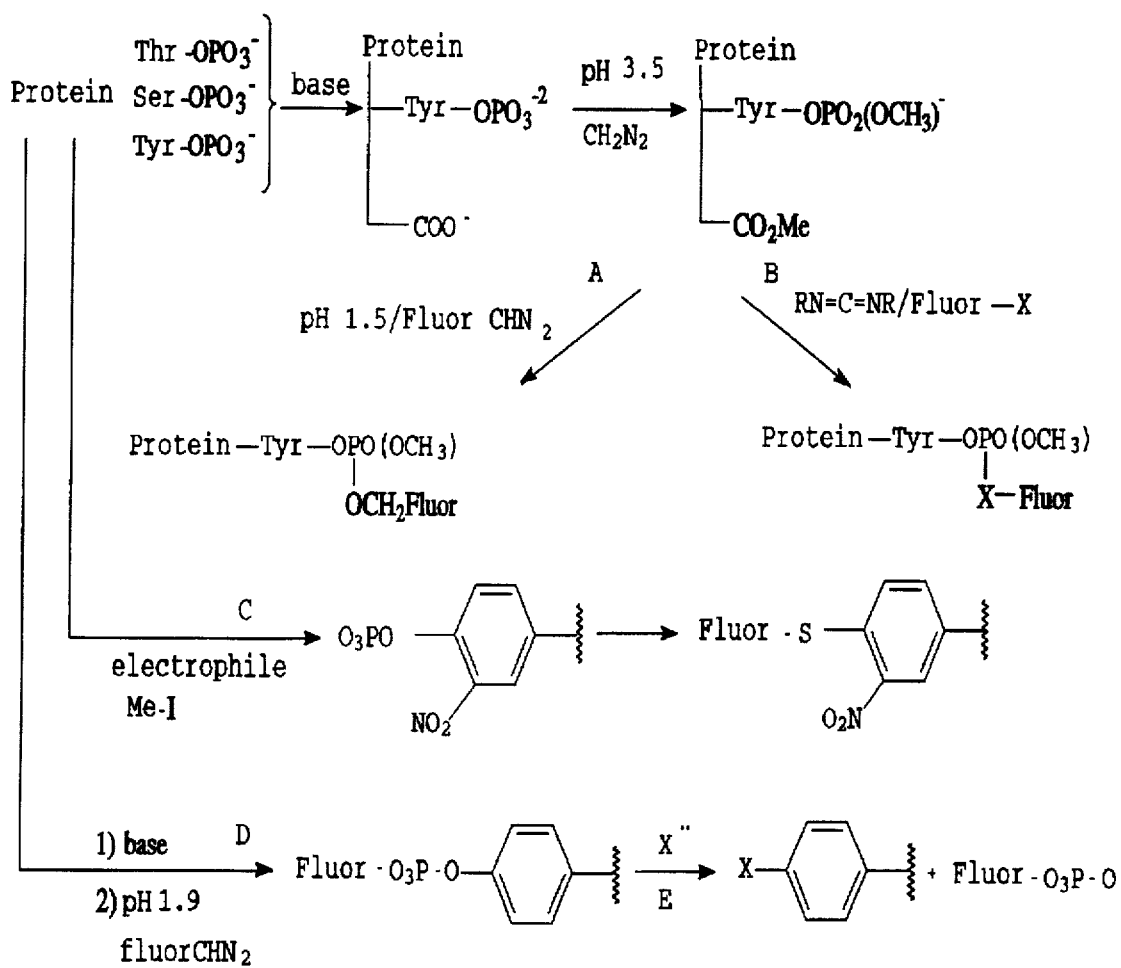
FIG. 2 provides a reaction scheme for derivatizing phosphotyrosine groups with a tag.

Four protocols for selective phosphotyrosine identification are described in FIG. 2.

The first two methods (A and B) rely on selective chemical modifications of the phosphoprotein/peptide which reveals a tyrosine phosphate moiety (Tyr-OP-OH) as the single reactive site in the modified protein/peptide. The selectivity of the chemical transformations rely on the base stability of the phosphotyrosine moiety and the low first pKa (≈1.7) of the phosphate group, which enables differentiation of the phosphate residue from the carboxylic acid sites. The initial differentiation of phosphotyrosine from phosphoserine and phosphothreonine residues is accomplished by treatment of the peptide with base sufficient to induce formation of the dehydroserine and threonine derivatives, about pH=14. Without initial base treatment, phosphothreonine and phosphoserine are also fluor tagged.

After removal of phosphoserine and phosphothreonine, acidification of the media to pH≈3.5 protonates the basic residues of the protein/peptide (arginine, lysine, histidine, N-terminus), the peptide carboxylic acid residues (pKa values generally range 4.25–6.00) and a single phosphate tyrosine monoester site. Subsequent reaction of the acidified peptide with a stable, unhindered diazoalkane (eg. diazomethane) or an aklylating agent, such as methyl iodide or methyl sulfate, reacts the protonated sites on the denatured peptide prone to reaction with the reagent. This treatment reveals the remaining hydroxylic moiety of the tyrosine alkane phosphodiester as the sole reactive groups (either P—OH or C—OH) in the peptide.

In one protocol (Method A), the phosphodiester is subjected to reaction with an electrophilic reagent such as a diazoalkane modification with a fluorescent diazoalkane species. After adjustment of the pH to≈1.50 the remaining phosphate site is protonated which enables reaction with the specific diazoalkane fluorophore.

In a second method (Method B), the phosphodiester is coupled to a fluorophore through standard coupling methodology. A diversity of coupling procedures which produce a range of phosphodiester derivatives (eg., ester, thioester, amide) can be utilized depending upon the detection method to be used. Activation of the single remaining active phosphate tyrosine monoester can be achieved with an activating groups such as a carbodiimide, an anhydride, an alkyl chloroformate, pyridinium salts-Bu$_3$N, phenyl dichlorophosphate, PhOPOCl$_2$, DCC and an aminopyridine, 2-chloro-1,3,5-trinitrobenzene and pyridine, polyphosphate ester, chlorosulfonlyl isocyanate, chlorosilanes, MeSO$_2$Cl—Et$_3$N, Ph$_3$P—CCl$_4$—Et$_3$N, and N,N'-carbonyldiimidazole. Attachment of the fluorophore can then be accomplished by reaction of the activated phosphate with a nucleophilic fluorophore.

The third group of methods (Method C) relies on ring modification of the phosphotyrosine moiety with an electron withdrawing group, which allows for selective substitution of the phosphotyrosine group by a fluorophore-containing nucleophile. Two complementary experimental protocols utilized for Method C, (C1) one involving conventional electrophilic aromatic substitution and another (C2) proceeding by addition of an electrophilic radical species (Scheme 2).

The sequence involving electrophilic aromatic substitution (C1) involves initial treatment of the protein/peptide with an electrophilic reagent (such as methyl sulfate, methyl iodide, 9 anthryldiazomethane, 1-pyrenyldiazomethane, 4-(diazomethyl)-7-methoxycoumarin, and 4-(diazometyl)-7-diethylaminocoumarin) under appropriate conditions (acidic methanol, at a pH of about 1.5–2.4, preferably about 1.9). Such manipulation serves to minimize the number of sites (such as SH, $NH_2$, OH and COOH) at which a species capable of electrophilic aromatic substitution (eg. a "$NO_2+$" species) could potentially react. Reaction of a representative nitrating electrophilic species at sites both in the side chain of the protein (eg. aromatic and possibly basic residues) and potentially in the backbone (amide) are feasible. However, reaction at the activated ortho-position of the phosphotyrosine results in a unique derivative, one capable of nucleophilic aromatic substitution. Thus, Method C entails initial modification of the peptide with an electrophile capable of blocking the nucleophilic thiol, amine and hydroxyl moieties of the peptide, followed by treatment with a nitrating species capable of electrophilic aromatic substitution, and subsequent nucleophilic aromatic substitution of the phosphoryl nitroaromatic (Scheme 2; pathway C). Suitable nitrating species for aromatic compounds include, nitric acid alone, or in water, acetic acid or acetic anhydride, methyl nitrate and $BF_3$, $NaNO_2$ and trifluoroacetic acid, $N_2O_4$ and nitronium salts such as $NO_2^+$ $BF_4^-$, $NO_2^+$ $PF_6^-$ and $NO_2^+$ $CF_3SO_3^-$.

A fourth method (Method D) is dependent on the radical addition to a phosphotyrosine arene, and quantitative release of the phosphate group.

The radical substitution methodology relies on established chemistry that demonstrates radical species, such as nitric oxide, undergo selective addition to aromatic amino acids (tyrosine, phenylalanine, tryptophan) in peptides. For example, nitrosophenylalanine has been identified as a modified amino acid, presumably derived from nitric oxide generated from either signaling or inducible (cytotoxicity) pathways. One pathway proceeds by analogy with the electrophilic pathway described earlier (pathway D). An alternate pathway involving a radical addition-elimination pathway (pathway E) releases the phosphate group. If the radical chemistry follows analogously to electrophilic aromatic substitution, the radical methodology provides a complementary and potentially more selective entry into the requisite intermediate for subsequent fluorophore introduction. However, if the alternate pathway (pathway E) predominates, the radical-based methodology provides a highly selective strategy for phosphotyrosine detection. Thus, since the phosphotyrosine moiety is the only derivative subject to phosphate release, this procedure entails coupling the phosphomonoester derivatives of the peptide with a fluorophore (as outlined above), followed by treatment with a suitable free radical, and monitoring release of the phosphorylated fluorophore. The method of pathway D relies on the exhaustive tagging of the protein with a fluorophore, followed, by quantitative removal of the fluorophorylated tyrosine groups by a free radical substitution and quantitative measurement of the amount of fluorophore liberated. Exhaustive fluorophorylation is conducted on the protein, which has been treated with base to eliminate the phosphoserine and phosphothreonine groups. Even though fluorophorylation will occur at both the phosphotyrosine groups and any carboxylic acid groups, liberation of the fluorophore is selectively performed on the fluorophorylated phosphotyrosine groups.

In addition, quantitative liberation of the fluorophore can also be conducted on the fluorophorylated proteins resulting from pathways A and B above, in which case the quantitative measurement of liberated fluorophore can be used as an confirmation of the amount of phosphotyrosine as determined by fluorescent methods on the fluorophylated protein.

Any compounds that interact with free thiol groups are attached to the activated serine residues (eg. iodoacetamide containing compounds such as iodoacetamidofluoroscein or biotin) and the phosphorylation state of a given protein or peptide in a complex mixture analyzed by conventional means such as capillary electrophoresis, hplc, mass spectrometry, SDS-PAGE and Western blotting. The work using phosphothreonine protein showed a lack of threonine participation in the alkaline β-elimination reaction at the reaction conditions stated, therefore the conditions we have defined are specific for phosphoserine containing peptides and proteins.

Analysis for the tag can also be accomplished by absorbance detection following chromatographic separation by conventional methods such as reverse phase HPLC, CZE and anion-exchange chromatography. While there are no particular limitations as to the different types of tags, which can be attached to the phosphoaminoacid, fluor tags are preferred, due to their ease of analysis. However, radioactive tags, which can be quantitatively measured for can also be attached.

Determination of Phosphothreonine

The amount of phosphothreonine in a phosphoprotein can be determined by first determining the total phosphorylation content of the protein, then determining the amount of phosphoserine and phosphotyrosine and assigning the remaining phosphate content as due to phosphothreonine.

Phosphorylation Mapping

The present invention also allows for the mapping of phosphorylation sites on a protein and peptide. In order to obtain a map of the phosphorylation sites, the protein is first sequenced by conventional means.

After the protein has been sequenced, the protein can be fragmented by conventional means, and the individual fragments subjected to identification for phosphoserine, and phosphotyrosine as described above. By identifying individual fragments with unique phosphorylation types, sequential fragmentation and identification can identify the specific serine, threonine or tyrosine unit which are phosphorylated. In such a manner, a map of the specific sites of phosphorylation can be obtained.

The present invention, to tag serine, threonine and tyrosine phosphorylated proteins and peptides has tremendous commercial potential in three areas: 1) diagnosis, 2) drug evaluation and 3) drug discovery. By attaching probes such as fluorophors or biotin to the activated phospho-amino acids on proteins and peptides one can analyze the phosphorylation states of cellular proteins (and peptides) derived from human or animal sources with tremendous sensitivity ($<10^{-20}$ molecules) utilizing capillary electrophoresis, hplc, mass spectrometry, SDS-PAGE or Western blotting. For example, the effects of new insulin-o-mimetic drugs can be evaluated directly in humans or animals by comparing their effects with insulin on the pattern of cellular protein phosphorylation. Specifically, in a clinical trial, subjects would be given a particular drug and needle biopsy taken from skeletal muscle and adipose tissue. The tissue is homogenized and centrifuged and the particulate fraction and soluble fraction subjected to the chemistries described above to activate the phospho-amino acids. Once activated the tissue samples are treated with Iodoacetamidofluoroscein which specifically tags all the phospho-amino acids in the samples with fluorescein. The samples are analyzed by capillary electrophoresis using laser induced fluorescence detection. An electrofluorogram is obtained on a data base which is essentially a finger print of the pattern of phosphorylation of proteins within the sample. The finger prints from each insulin-o-mimetic drug tested can be compared with tissue samples derived from subjects treated with insulin. Thus, using the present invention, in the example cited, one can get an accurate assessment on how useful a drug is likely to be as a replacement for natural insulin.

The fact that the chemistries are simple opens the door to automation making the invention a valuable tool in screening programs trying to identify new drugs that effect cells by altering their intracellular protein phosphorylation state eg. anti cancer drugs, insulin-o-mimetic drugs or antihypertensive drugs. For example, a particular tumor cell line of known origin is grown in 96 well titre plates. The tumor cells are treated with variety of compounds robotically and the titre plates treated with homogenization buffer. The cells are lysed and the titre plates centrifuged. The cell extracts are then treated with the chemistries outlined above to activate phosphoamino acids. The cellular phospho-proteins are then tagged midi a fluorophor as outlined earlier and the phospho protein finger print pattern determined by capillary electrophoresis with laser induced fluorescence detection. This analysis could also be carried out on a larger scale by adapting an automated DNA sequencer that use laser induced fluorescence detection. This way up to 40 samples can be finger printed simultaneously. Finger print patterns induced by a particular compound that closely match the phospho-protein finger print obtained from normal cellular phenotype will strongly indicate that compound may have tumor suppressive properties.

The present invention is also a useful tool for those researching the causes of disease states, such as cancer and diabetes. Current hypothesis as to the causes of these disease are that they are the result of selective defects in signal transduction pathways controlling normal cellular function. By comparing the phospho-protein finger print pattern obtained from a particular cancer cell for example with a normal cell one can identify specific molecules that are defective in their phosphorylation state. Such findings are of great importance in establishing the causes of these disease and ultimately to finding cures.

Having generally described this invention, a further understanding can be obtained by reference to certain specific examples which are provided herein for purposes of illustration only and are not intended to be limiting unless otherwise specified.

EXPERIMENTAL PROCEDURES

The following describes the protocols followed in the activation of phosphoserine on a chymotryptic/tryptic fragment of recombinant smooth muscle chicken gizzard light chain. These reaction conditions will also work for phosphoserine residues on any protein or peptide regardless of surrounding amino acid sequence. In the protocol described fluorescein was subsequently attached to the activated amino acid. Other iodoacetate containing compounds could also be used, e.g., other fluors or biotin.

Materials

All analysis was carried out by capillary electrophoresis and performed on a Beckman P/ACE System 2100. On-line laser induced fluorescence detection was accomplished using a Beckman P/ACE LIF detector and UV absorbance with a Beckman P/ACE UV absorbance detector. fused-silica capillaries, 50 mm inner diameter by 57 cm long. All chemicals were purchased from Aldrich Chemical Company, Inc., USA, except the fluorescent probe Iodoacetamidofluoroscein (U-15), which was purchased from Molecular Probes, Inc., Eugene, Oreg.

EXAMPLE 1

A. 1,2-Ethanedithiol Derivatization of Serine Phosphopeptide

The phosphopeptide (Ala-Thr-SerP-Asn-Val-Phe) was derivatized by a much modified reaction mechanism used by Clark and Dijkstra (1967), *Int., J., Biochem.*, 11, 577–585. and Meyer, et al (1986), *FEBS*, 204, 61–66. for stabilizing phosphoserine residues during Edman degradation reactions. 40 ml of 0.236/g/ml phospho peptide was dried completely in a Speedvac (Savant) and derivatized by the addition of 50 ml reaction mixture under nitrogen and incubated for 60 minutes at 55° C. The reaction mixture contained 200 ml dd$H_2O$, 65 ml 5N NaOH, 6 ml EDTA, 245 ml DMSO, 90 ml ethanol, 125 ml 1,2-ethanedithiol (EDT), all components thoroughly gassed With nitrogen. The reaction was stopped with 1 ml of 1.75M acetic acid. The derivatized peptide was applied to a C-18 Sep-Pak cartridge (Waters) and eluted with 50% ACN and concentrated. The derivatized peptide was analyzed on CZE.

B. Fluorescent Tagging of Derivatized Peptide

The derivatized peptide, in 14 ml volume, was incubated with 4 ml of I-15 1.0 mg/ml in the dark of 90 minutes and analyzed on CZE under the same conditions as above.

EXAMPLE 2

Derivatization of Phosphothreonine Residues with EDT

There was some question as to whether phosphothreonine proteins would also react with EDT under the same reaction conditions, so similar work was done on $^{32}P$ labeled myelin basic protein (MBP) labeled on threonine. Under the same reaction conditions as the phosphorylated MLC20, MBP did not release $^{32}P$ at an adequate level. It was assumed that a higher concentration of hydroxyl ions were required to remove the hydrogen from the a carbon in order to start the reaction.

Reaction conditions were changed to 2M EDT and phosphate release was increased dramatically. A reaction time course using the 2M EDT conditions was performed from 40 minutes to 110 minutes and these samples were run on an SDS PAGE with an auto radiograph made of the gel. Degradation of the protein, even at 40 minutes, suggests the reaction conditions were too harsh for the peptide bond to stay intact.

EXAMPLE 3

(1) Measurement of the phosphorylation state of smooth muscle myosin light chain 20 (MLC20) by CZE and LIF.

Fluorophore tagging of phosphate residues on amino acids utilized a modification of the method used to stabilize phosphoserine during Edman sequencing. Our test model for these studies was the peptide Ala-Thr-SerP-Asn-Val-Phe, the serine 19 phosphorylation site of MLC20 (Fadden and Haystead, T.A.I. Analytical Biochemistry (1995)). This work demonstrated that fluorophore tagging of peptides and proteins via their phosphoamino acids enabled quantitative determinations of phosphorylation to be made at the attomole level.

Having defined conditions in which the phosphoserine content of a protein or peptide could be determined in vitro, the methodology was utilized to measure phosphorylation events occurring in vivo. Our first experiment was to peptide map and quantitate smooth muscle MLC20 phosphorylation in vivo.

A chromatogram shows the presence of a fluorescent peptide migrating at 5.55 minutes in the sample derived from the contracted bladder and that this peptide is completely absent in the sample derived from relaxed bladder. The migration of the 5.55 peptide corresponds to the purified peptide Ala-Thr-SerI15-Asn-Val-Phe. These results are consistent with phosphorylation of MLC20 in response to carbachol and dephosphorylation of MLC20 with muscle relaxation. Importantly, our ability to measure changes in the phosphorylation state of MLC20 in vivo, indicate that under the reaction conditions described, labeling of phosphoserine in complex peptide mixtures proceeds as observed with a purified phosphopeptide.

In separate experiments the stoichiometry of MLC20 phosphorylation was determined in response to carbachol. One of the useful features of MLC20 is that it contains a single cysteine residue (*Cys 109), which can be labeled with I-15 fluorophor. The migration of the tryptic/chymotryptic fragment containing Cys 109 was determined on CZE using a Cys 109 fluor tagged peptide from purified recombinant MLC20 as a standard. Quantitation of the Cys 109 peptide content of the tryptic/chymotryptic digests was used as a measure of the tissue concentration of MLC20 in pig bladder (70±15 µM; SDM, N=3), and hence, the stoichiometry of MLC20 phosphorylation following carbachol treatment (0.82±0.12 mol/mol; SDM, N=3). Therefore, when working with purified proteins, if the cysteine content is known, fluorophore tagging of these residues can be used as an accurate measure of protein concentration.

EXAMPLE 4

Identification of the in vivo phosphorylation sites in 130 kDa subunit of smooth muscle protein phosphatase-1M (SMPP-1M) by LIF and Edman sequencing reaction. In vertebrate smooth muscle and non-muscle cells, $Ca_{+2}$ regulation of contraction is due to phosphorylation of MLC20 by myosin light chain kinase (MLCK) (Somlyo and Somlyo, 1994 Nature, 372: 231–236. Hence, dephosphorylation of MLC20 is requisite for relaxation. Although the mechanism of MLC20 phosphorylation has been well studied, the mechanism of regulation of its dephosphorylation is unknown. My laboratory recently purified and characterized, from intact pig bladder, the mammalian form of SMPP-1M (Shirazi et al. 1994 J. Biol. Chem. 269: 31598–31606. SMPP-1M consists of three subunits, the 37 kDa catalytic subunit of phosphatase 1 (PP-1C), a 130 kDa myosin binding fibers have indirectly provided evidence to suggest that SMPP-1M activity is regulated in vivo via a G protein-mediated-signal transduction pathway. However, the inherent problems associated with $^{32}P$-labeling of intact muscle fibers and tissue has precluded studies that directly measure whether SMPP-1M activity is regulated by phosphorylation of its subunits. To address this question, SMPP-1M was isolated from contracted or relaxed pig bladders. The purified enzymes wire digested with trypsin and the proteolytic fragments derivatized, tagged with fluorophor then characterized by CZE and LIF.

The results in Table 1 shows that carbachol increased the fluorescence of four SMPP-1M peptides (I–IV) migrating at 4.50, 6.84, 10.40 and 11.62 minutes relative to the EGTA sample. A single peptide (V) eluting at 12.60 minutes appears reduced in fluorescent content relative to the EGTA sample. These results indicate that in response to carbachol SMPP-1M is enhanced in serine phosphorylation at least four distinct sites, and possibly dephosphorylated at a fifth site. Or the fifth site is selectively enhanced in its phosphorylation following EGTA treatment, but does not change with carbachol.

TABLE 1

| Peptide | Carbachol | EGTA | Fold change |
|---|---|---|---|
| I | 35 ± 9 | 14 ± 2 | 2.5 ± 0.3 |
| II | *105 ± 34 | 11 ± 3 | 9.5 ± 3.2 |
| III | 28 ± 15 | 9 ± 3 | 3.1 ± 1.8 |
| IV | 16 ± 7 | 2 ± 0.5 | 8.0 ± 3.5 |
| V | 14 ± 5 | 45 ± 9 | –3.2 ± 1.0 |

*peptide II is the sum of 3 closely migrating peptides.

Effects of carbachol and EGTA on the phosphoserine content of pig bladder SMPP-1M. Results shown are mean of three separate experiments (±SDM) in which SMPP-1M was isolated from carbachol and EGTA treated pig bladders. Fluoropeptide analysis was carried out by CZE and LIF following derivatization with EDT or SMPP-1M digests. Peak areas (in arbitrary units (a.u.)) of individual peptides were integrated using Beckman system gold software. Subsequent amino acid sequencing indicates peptide II may contain varying amounts phosphothreonine or tyrosine, explaining its heterogeneity.

To determine which subunit in SMPP-1M is phosphorylated and the nature of the protein kinases(s) that bring about these phosphorylations, peptides I–V were purified by HPLC using fluorescence for detection. The amino acid sequence of the peptides was determined by Edman sequencing (Table 2) and showed they were derived from the C terminal half of the 130 kDa subunit of SMPP-1M. Several protein kinase consensus phosphorylation sites are present, including sites for protein kinase C, cyclic AMP and cyclic GMP dependent protein kinase. Significantly, as shown in Table 2, the absence of serine in several places in these peptides is consistent with conjugated of this amino acid with I-15. This was directly confirmed in peptide I by following protocols similar to that described by Stoke et al. (1992) Eur. Mol. Biol. J., 11: 3985–3994. for the identification of $^{32}P$-phosphoserine in peptides. The appearance of fluorescence following six cycles of Edman degradation of peptide I is consistent with fluorophore tagging of serine 781 in the 130 kDa subunit of SMPP-1M. These results demonstrate that fluorophore tagging of phosphoamino acids not only allows one to peptide map phosphorylation sites on a given protein, but also by Edman sequencing, identifying the exact position of the fluoroamino acid (and hence precise phosphorylated amino acid). It is anticipated that a similar approach will allow identification of the position of fluorothreonine and fluorotyrosines in phosphorylation sites on proteins (see Program Design/Methods).

TABLE 2

| Peptide | Amino Acid Sequence | Position in 130kDa | Molecular Mass |
|---|---|---|---|
| I | EGEDKXQPK | 775–784 | *1548.5 |
| II | KEXEVXREDEYK | 689–700 | *2494.62 |
| III | ? | ? | 1761.23 |
| IV | RXYLTPVR | 611–618 | *1487.54 |
| **V | ? | ? | 1695.3 |

*Molecular masses include addition of fluorophoreI-15 to the side chain α carbon of serine and were determined by laser desorption mass spectrometry. X indicates serine was absent from sequence. Peptide position in amino acid sequence of the 130kDa subunit was determined from the published sequence of rat smooth muscle aorta SMPP-1M (Chen et al. 1994).
**peptides III and V have yet to be sequenced.

Table 2. Amino acid sequences of the major phosphoserine containing peptides in SMPP-1M isolated from carbachol treated pig bladder.

EXAMPLE 5

Measurement of glycogen synthase and phosphorylase phosphorylation in diabetic and non-diabetic rat skeletal muscle.

Measurements on phosphoproteins are made in complex extracts derived from animal and human tissue samples containing <100 cells to test the effects of the diabetic state on the phosphorylation of glycogen synthase and phosphorylase in vivo.

Two proteins migrating at 86 kDa and 96 kDa in the electropherogram, identified as glycogen synthase and phosphorylase respectively, show dramatic changes in phosphorylation state between the two conditions. In the normal fed rat, endogenous insulin levels are raised and the phosphorylation state of glycogen synthase (86 kDa) was decreased by 20±5.8% (SDM. N=4), compared with that in the diabetic animals. Earlier studies in rabbit skeletal muscle demonstrated glycogen synthase to contain at least ten serine phosphorylation sites (Cohen, 1986). However, only three of these (serine 30, 34 and 38) are thought to be insulin sensitive In our experiments, a 20–25% reduction in overall synthase phosphorylation in the normal animal is consistent with dephosphorylation of two or more of these sites. More dramatic changes in phosphorylation state between diabetic and non-diabetic were observed with phosphorylase (96 kDa). The peak eluting at 96 kDa in the diabetic state is almost completely absent in the non-diabetic state. Activation of phosphorylase occurs by its phosphorylation by phosphorylase kinase (Nolan et al. 1964), which is its self phosphorylated and activated by cyclic AMP dependent protein kinase. In the presence of insulin, intracellular cyclic AMP levels would be depressed, thus favoring dephosphorylation of phosphorylase.

Although the most dramatic changes are due to phosphorylase and glycogen synthase phosphorylation, expansion of the y axis reveals a more complicated pattern of phosphorylation between the two samples. For example, proteins eluting at 6 kDa 20 kDa, 70 kDa appear to increase in phosphorylation in the diabetic sample with respect to the normal. Whereas, proteins eluting at 25 kDa and 50 kDa appear to increase in the normal sample relative to the diabetic state. By contrast proteins eluting between 30 and 40 kDa do not appear to change in either case. The identity of these other phosphoproteins has yet to be determined, however, multiple measurements of protein phosphorylation events can be achieved by fluorescence labeling in complex mixtures.

Although we are able to discriminate several phosphoproteins by SDS-gel capillary electrophoresis and LIF, the resolution obtained is poor compared with conventional SDS-gel electrophoresis. An autoradiogram of an SDS-gel of muscle extract prepared from $^{32}$P-labeled muscle would show many more phosphoproteins than resolved in our experiment This is because SDS-gel capillary electrophoresis is a compromise between SDS-gel electrophoresis and CZE. Capillary zone electrophoresis is an excellent method for resolution of peptide mixtures, but not useful for separation of complex protein mixtures. However, if one can combine the excellent resolving power of conventional SDS-gel electrophoresis with LIF, excellent resolution and quantitation of fluorophor tagged proteins in complex mixtures can be obtained. For this proposal we have adapted an Applied Biosystems automated DNA sequencer to separate fluor-tagged proteins. The major requirement for this adaptation is to utilize 12–15% polyacrylamide, rather than 4% in the separating gel. In addition, the Applied Biosystems automated DNA sequencer is capable of analyzing 4 separate fluors simultaneously. Therefore, one will be able to attach different colored fluors to phosphoserine, phosphotyrosine and phosphothreonine and quantitate them simultaneously. In addition, a fourth fluor can be attached to cysteine residues for measuring protein concentration.

Obviously, numerous modifications and variations of the present invention are possible in light of the above teachings. It is therefore to be understood that within the scope of the appended claims, the invention may be practiced otherwise than as specifically describe herein.

What is claimed as new and desired to be secured by Letters Patent of the United States is:

1. A method for determining the amount of phosphoserine in a protein comprising:
   a) reacting a phosphoprotein with a thiol linker under reaction conditions to effect derivatization of phosphoserine groups in said protein with said thiol linker;
   b) reacting said thiol linker of said derivatized protein with a fluorescent tag;
   c) quantitating the amount of said fluorescent tag.

2. The method of claim 1, wherein said thiol linker is ethanedithiol.

3. The method of claim 1, wherein said fluorescent tag is monitored by capillary zone electrophoresis.

4. The method of claim 1, wherein said thiol linker is an alkyldithiol having 2 to 12 carbon atoms or an aryldithiol.

5. The method of claim 1, wherein said thiol linker is an alkylpolythiol having 2 to 12 carbon atoms or an arylpolythiol.

6. A method for determining the amount of phosphotyrosine in a protein comprising:
   a) reacting a protein with base at pH 14, to remove the phosphates from phosphoserine and phosphothreonine residues;
   b) acidifying said reaction mixture to pH about 3.5;
   c) reacting said acidified peptide with an alkylating agent;
   d) acidifying said reaction mixture to pH about 1.5 to form an acidified phosphonodiester of a phosphotyrosine;
   e) reacting said acidified phosphonodiester of a phosphotyrosine with a fluorescent tag; and
   f) quantitating the amount of said fluorescent tag.

7. The method of claim 6, wherein said fluorescent tag is a fluorescent diazoalkane.

8. The method of claim 6, wherein said fluorescent tag is a fluorescent coupling agent.

9. The method of claim 6, wherein said alkylating agent is a diazoalkane.

10. A method for determining the amount of phosphotyrosine in a protein comprising:
   a) reacting a protein with an electrophilic reagent under appropriate conditions to react SH, $NA_2$, OH and COOH groups;
   b) reacting a phosphotyrosine moiety in said protein with a species capable of electrophilic aromatic substitution;
   c) reacting said substituted aromatic with a fluorescent nucleophile; and
   d) determining the amount of said fluorescent nucleophile.

11. A method for determining the amount of phosphotyrosine in a protein comprising:
   a) reacting a protein with a base to remove the phosphates from phosphoserine and phosphothreonine residues;
   b) reacting said protein of step a) with a fluorophor; and
   c) reacting said fluorophorylated protein with a free radical; and
   d) quantitating the release of fluorophosphate.

12. A method for mapping the phosphorylation state of serine and tyrosine residues in a protein comprising:
   a) determining the amino acid sequence of a protein;
   b) fragmenting said protein;
   c) determining the presence of phosphoserine and phosphotyrosine residues in said fragments; and
   d) correlating the presence of phosphoserine and phosphotyrosine residues with the sequence of said protein.

* * * * *